United States Patent [19]

Schiessler et al.

[11] Patent Number: 4,684,753

[45] Date of Patent: Aug. 4, 1987

[54] PROCESS FOR PREPARING 1,3,6,8-TETRABROMOPYRENE

[75] Inventors: Siegfried Schiessler, Bad Soden am Taunus; Ernst Spietschka, Idstein, both of Fed. Rep. of Germany

[73] Assignee: Hoecsht Aktiengesellschaft, Fed. Rep. of Germany

[21] Appl. No.: 907,400

[22] Filed: Sep. 12, 1986

[30] Foreign Application Priority Data

Sep. 14, 1985 [DE]  Fed. Rep. of Germany ....... 3532882

[51] Int. Cl.$^4$ .............................................. C07C 17/02
[52] U.S. Cl. .................................................... 570/206
[58] Field of Search ........................................ 570/206

[56] References Cited

FOREIGN PATENT DOCUMENTS 937646  7/1953  Fed. Rep. of Germany .

OTHER PUBLICATIONS

Vollman et al., *Ann.* 531, pp. 12 and 16 (1937).

*Primary Examiner*—J. E. Evans
*Assistant Examiner*—Joseph A. Boska
*Attorney, Agent, or Firm*—Connolly and Hutz

[57] ABSTRACT

Process for preparing 1,3,6,8-tetrabromopyrene by brominating pyrene in aqueous suspension with simultaneous reoxidation of the resulting hydrogen bromide to bromine by means of an oxidizing agent, which comprises reacting pyrene in a highly concentrated aqueous suspension having a pyrene-water weight ratio of 1:1.2 to 2 with bromine at temperatures of 40° to 65° C. with simultaneous reoxidation of the resulting hydrogen bromide to bromine using an oxidizing agent, completing the bromination by heating the reaction mixture to temperatures of 70° to 130° C., reducing excess bromine with a reducing agent to hydrogen bromide and subjecting the 1,3,6,8-tetrabromopyrene formed, preferably without intermediate isolation, to an alkaline aftertreatment at temperatures of 40° to 100° C. within the pH range 8.5 to 12.

7 Claims, No Drawings

PROCESS FOR PREPARING 1,3,6,8-TETRABROMOPYRENE 1,3,6,8-Tetrabromopyrene of the formula (1) is an important intermediate in the preparation of naphthalene-1,4-5,8-tetracarboxylic acid.

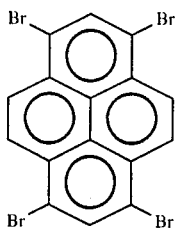

(1)

As is known [Annalen 531 (1937), 12], the preparation of 1,3,6,8-tetrabromopyrene can be effected by brominating pyrene in suitable inert solvents, such as, for example, nitrobenzene or trichlorobenzene, at elevated temperature. Yet this process is not economical, since working with such solvents requires very high technical expenditure, not least for physiological and ecological reasons.

Furthermore, it is known from German Pat. No. 937,646 that pyrene can be brominated in an aqueous medium to 1,3,6,8-tetrabromopyrene and that, in said reaction, to reduce the amount of bromine the hydrogen bromide which is formed in the course of bromination can be reoxidized to bromine by means of an oxidizing agent. This process is indeed of interest, but its implementation is not economically feasible since the pyrene needs to be subjected to very expensive roll milling before the bromination. In addition, this process requires the use of surface-active compounds and of sulfuric acid, as a result of which the process of isolating tetrabromopyrene produces polluted filtrates. Moreover, the tetrabromopyrene obtained in accordance with German Pat. No. 937,646 on filtration, despite thorough washing of the filter cake with water, still gives off hydrogen bromide on drying, as a result of which there are considerable corrosion problems in the drying apparatuses and also waste air problems.

A further disadvantage of the process described in German Pat. No. 937,646 is that 100% pure pyrene is used for the reaction. However, such a grade of pyrene, owing to the extraordinarily high manufacturing costs, is not usable for an economical process.

In addition, in the course of repeating the previous work it was found that the theoretical yield given in German Pat. No 937,646 was merely calculated from the weight increase of the pyrene during the bromination and that the true yield is below 90% of theory. The cause of this discrepancy is that brominated pyrene, in contradiction to the statements in the literature [Annalen 531 (1937), page 16], can also form addition compounds with bromine and that the increase in weight which then occurs suggests a higher yield of tetrabromopyrene than is obtained in reality.

It has now been found that 1,3,6,8-tetrabromopyrene of the abovementioned formula (1) can be prepared in an aqueous medium in a technically simple and ecologically safe manner while avoiding the defects associated with the known processes mentioned, and in a higher yield, by reacting pyrene, in particular technical-grade crude pyrene, in a highly concentrated aqueous suspension having a pyrene water weight ratio of 1:1.2 to 2, preferably 1:1.5 to 1.7, with bromine at temperatures of 40° to 65° C., preferably 45° to 55° C., with simultaneous reoxidation of the resulting hydrogen bromide to bromine using an oxidizing agent, completing the bromination by heating the reaction mixture to temperatures of 70° to 130° C., preferably 85° to 100° C., reducing excess bromine with a reducing agent to hydrogen bromide, and subjecting the 1,3,6,8-tetrabromopyrene formed, preferably without intermediate isolation, to an alkaline aftertreatment at temperatures of 40o to 100oC within the pH range 8.5 to 12.

Suitable oxidizing agents for reoxidizing the hydrogen bromide formed in the course of bromination of pyrene with bromine are for example the alkali metal and alkaline earth metal hypochlorites, hypobromites, peroxodisulfates, chlorates and bromates, preferably alkali metal chlorates, such as sodium chlorate. The bromine produced in the course of the reoxidation of the hydrogen bromide formed immediately re-enters the process of bromination, as a result of which the starting amount of bromine can be kept significantly lower.

Suitable reducing agents for reducing excess bromine to hydrogen bromide are for example sulfur dioxide and also salts of sulfurous acid, i.e. sulfites and bisulfites, preferably the alkali metal and alkaline earth metal sulfites and bisulfites, in particular the sodium salts. Gaseous sulfur dioxide is advantageous insofar as it is capable of reducing the bromine contained in coarsely grained tetrabromopyrene in the form of inclusions to hydrogen bromide.

The pyrene used is preferably the commercially available, technical-grade crude pyrene which is obtained in the fractional distillation of coaltar and which customarily has a purity of 85-95%. This crude pyrene contains a number of impurities which have a vapor pressure comparable to pyrene, of which brazan and fluoranthene are the main components. These impurities are likewise polybrominated in the course of the bromination. Brazan, which, as the main impurity in technical-grade pyrene, is present in an amount of 2-10%, is for example tetra- to pentabrominated.

To effect bromination in highly concentrate aqueous suspension, the technical-grade crude pyrene is customarily first suspended in 1.2 to 2 times, preferably 1.5 to 1.7 times, the amount by weight of water (based on pyrene used) and then brominated. The amount of water is limited at the lower end by the fact that the bromination suspension must still be stirrable. Since the formation of the tetrabromopyrene is associated with a considerable increase in weight, the bromination suspension contains a solids content of above 50% toward the end of the bromination.

The amount of bromine for the bromination, bearing in mind the bromine formed by reoxidation, is decided in such a way that an excess of bromine is present throughout the entire bromination. However, in deciding the amount of bromine on that basis care needs to be taken that toward the end of the reaction only a small excess of bromine is left over, since otherwise, through addition of 1-2 moles of bromine onto the tetrabromopyrene, undesirable bromine addition compounds can be formed. The starting amount of bromine also depends on the nature and amount of the oxidizing agent used to reoxidize the hydrogen bromide formed to bromine.

It is expedient to use 1.6 to 2 times, preferably 1.7 times, the amount by weight of bromine, based on the crude pyrene used, for the bromination according to the invention.

Since the tetrabromopyrene, after prior treatment with one of the abovementioned reducing agents for removing excess bromine, and even after a thorough wash of the product isolated by filtration, gives off hydrogen bromide on drying, as a result of which corrosion and waste air problems arise, the alkaline aftertreatment according to the invention of the tetrabromopyrene in the reaction mixture obtained is required. To this end, preferably the reaction mixture obtained is initially brought to pH 6-10 by adding an alkali metal hydroxide, preferably sodium hydroxide, expediently in the form of an aqueous solution. Ammonia, in gas form or in the form of an aqueous solution, is then added, and the reaction mixture is subjected for several hours to the aftertreatment at temperatures of 40° to 100° C., where appropriate in a sealed vessel. The tetrabromopyrene thus aftertreated does not give off any corrosive compounds, such as hydrogen bromide, on drying.

It is true that the alkaline aftertreatment of the tetrabromopyrene can also be effected by initially isolating the tetrabromopyrene and then subjecting it in a second stage to an alkaline aftertreatment, but preference is given to the alkaline aftertreatment of the suspension obtained (reaction mixture) without intermediate isolation of the tetrabromopyrene.

DESCRIPTION OF FURTHER DETAILS OF PRACTISING THE PROCESS

In the case of using chlorates as reoxidizing agents, the amount added is fixed in such a way that all of the chlorate has been consumed by the end of the bromination. The chlorate can be added in the course of the bromination in small portions or continuously, but the addition of the entire amount of chlorate before the start of the bromination is preferred. The chlorate can be added not only in solid form but also in the form of concentrated aqueous solution. In the case of using an aqueous chlorate solution, the amount of water used for suspending the pyrene must be correspondingly reduced in order to ensure the requisite high concentration of the pyrene suspension. In terms of temperature control, the bromination is carried out in its preferred form in such a way that after addition of the sodium chlorate to the aqueous pyrene suspension the bromine is gradually added at a temperature of 40° to 65° C., preferably at 45° to 55° C., with slight cooling and the addition is followed by a period of stirring within the temperature range mentioned. At this reaction temperature both the bromination and the reoxidation of the resulting hydrogen bromide to bromine proceed relatively rapidly. In contrast, the bromination at a lower temperature, in particular on using chlorates as oxidizing agents, has the disadvantage that the reoxidation of the hydrogen bromide proceeds too slowly and the subsequent heating of the bromination mixture leads to a sudden increase in the rate of reaction with a pronounced increase in temperature. However, an increase in temperature above 65° C., in particular at the start of bromination, is absolutely to be avoided, since otherwise irreversible formation of lumps occurs and prevents successful bromination. To complete the bromination the reaction mixture is subsequently heated at 70° to 130° C. for several hours. Although this can be effected under pressure in a sealed vessel, preference is given to completing the bromination under atmospheric pressure, by refluxing.

After bromination has ended, the bromination suspension, which owing to the presence of hydrobromic acid is strongly acidic, is preferably diluted with water and the excess bromine, where appropriate after prior removal of the bulk of the bromine by distillation, is reduced to hydrogen bromide by adding a reducing agent.

The advantage of the claimed process over the process of German Pat. No. 937,646 consists in the following points:

(1) A significantly better yield of 1,3,6,8-tetrabromopyrene is obtained; a very high space-time yield is also achieved;

(2) owing to the high concentration employed, the technically very expensive milling of the pyrene before the start of the bromination can be dispensed with;

(3) the waste water produced in the course of the filtration of the tetrabromopyrene is not contaminated by surfactants and sulfuric acid;

(4) corrosion problems in the drying of the tetrabromopyrene disappear;

(5) starting from the tetrabromopyrene prepared by the process according to the invention, the further processing to naphthalene-1,4,5,8-tetracarboxylic acid gives a yield of this compound, based on the pyrene used, which is at least 5% higher than in the case of the tetrabromopyrene prepared as described in German Pat. No. 937,646.

The process according to the invention is new. It was not foreseeable that bromination in highly concentrated aqueous pyrene suspension without any prior fine division gives a higher yield of 1,3,6,8-tetrabromopyrene than the process described in German Pat. No. 937,646.

The 1,3,6,8-tetrabromopyrene obtained using the claimed process finds utility as an organic intermediate, in particular for preparing naphthalene-1,4,5,8-tetracarboxylic acid or the monohydride thereof.

The parts and percentages mentioned in the examples are by weight.

EXAMPLE 1

(a) 220 parts of technical-grade pyrene having a purity of 90% (brazan concent about 6%) are stirred into a solution of 84 parts of sodium chlorate in 360 parts of water. 371 parts of bromine are then added dropwise at 45°-55° C. with slight cooling in the course of 1½ to 2 hours. This is followed by stirring at 45°-55° C. for 1 to 2 hours. The temperature is then gradually raised under reflux conditions to 85°-95° C., which is followed by stirring at 85°-100° C. for 8 hours. The initially still prominent bromine reflux disappears almost completely in the course of the reaction. After the reaction has ended, the suspension is diluted with 280 parts of water, and the temperature is allowed to drop to 60°-70° C. The excess bromine is then removed by gradual addition of about 30 parts of 40% strength sodium sulfite solution. The suspension is then brought by addition of about 25 parts of 33% strength sodium hydroxide solution to pH 6.5-7.5. 40 parts of the aqueous 25% strength ammonia solution are then added, and a pH value of 9-10 becomes established. This is followed by stirring at 60°-70° C. and, finally, by filtration with suction, washing with water until salt-free and drying at 100° C. On drying the product does not give off any hydrobromic acid.

The 1,3,6,8-tetrabromopyrene (bromine content: 61.7%) is obtained in an amount of 558 parts and a purity of about 83%. This corresponds, based on 100% pure pyrene, to a yield of about 91% of theory. On further processing this tetrabromopyrene to naphthalene-1,4,5,8-tetracarboxylic acid by hydrolysis in oleum, and subsequent hypochlorite oxidation of the isolated intermediate, 252 parts of naphthalene-1,4,5,8-tetracarboxylic 1,4-monoanhydride are obtained, which corresponds to a yield of 89.9% of theory based on 100% pure pyrene.

The purity of the technical-grade tetrabromopyrene is determined by utilizing the fact that the impurities, unlike 1,3,6,8-tetrabromopyrene, are very readily soluble in o-dichlorobenzene, using the following method:

50 parts of the tetrabromopyrene obtained in Example 1a are added in finely milled form to 1000 parts of o-dichlorobenzene, which is followed by stirring at 160°-1700° C. for 2 hours. This is followed by cooling down to 60°-70° C. and filtration with suction at that temperature. The filter cake is washed with 500 parts of o-dichlorobenzene. The filter cake is then washed with methanol until free of o-dichlorobenzene and is dried at 100° C. This leaves 41.4 parts of pure tetrabromopyrene.

(b) Using in the bromination described in Example 1a instead of 371 parts of bromine a bromine quantity of only 340 parts gives only 540 parts of 1,3,6,8-tetrabromopyrene having a purity of only about 74%. This corresponds, based on 100% pure pyrene, to a yield of about 79% of theory.

(c) On using in the bromination described in Example 1a instead of 371 parts of bromine a bromine quantity of 420 parts, it is found that a very large excess of bromine is still present even toward the end of the bromination. The tetrabromopyrene is obtained in an extremely coarsely grained and specifically very heavy form which is technically very difficult to handle. It is true that in this case, as a consequence of the addition of bromine onto the tetrabromopyrene, a yield of 578 parts of "tetrabromopyrene" (bromine content 64-65%) is obtained, but on further processing only 243 parts of naphthalene-1,4,5,8-tetracarboxylic acid 1,4-monoanhydride are produced.

(d) On dispensing before the isolation of the tetrabromopyrene with the ammonia aftertreatment and on isolating the tetrabromopyrene from the neutral suspension by filtration and washing it thoroughly with water, drying still sets free hydrogen bromide which constitutes a significant waste air pollutant and leads to the corrosion of the drying apparatus.

EXAMPLE 2

(Repeat of Example 2 of German Pat. No. 937,646)

220 parts of technical-grade pyrene having a purity of 90% (identical to the pyrene used in Example 1) are rollmilled for 96 hours with 6.6 parts of sodium dibutylnaphthalenesulfonate and 440 parts of water. The suspension is rinsed with 880 parts of water into a flask. 374 parts of bromine are then added dropwise at 20°-30° C. in 2 hours. After disappearance of the bromine color, 74.8 parts of 100% strength sulfuric acid are added. After heating to 60° C., a solution of 72.9 parts of sodium chlorate in 330 parts of water is added dropwise at 60°-70° C. in 5 hours. The temperature is then raised to 85°-90° C. and is maintained at 85°-90° C. for 11 hours. Cooling down is followed by filtration with suction, washing with water until neutral and drying at 100° C.

Hydrogen bromide is liberated during the drying. The 1,3,6,8-tetrabromopyrene is obtained in an amount of 544 parts and in only 73% purity. This corresponds, based on 100% pure pyrene, to a yield of about 78% of theory.

EXAMPLE 3

(a) 220 parts of technical-grade pyrene of 93% purity (brazan content 4%) are added to a solution of 84 parts of sodium chlorate in 340 parts of water. 375 parts of bromine are then added dropwise at 40°-50° C., with slight cooling, in 2 hours. This is followed by stirring at 40°-50° C. for 1-2 hours. The temperature is then gradually raised with reflux cooling to 85° C., which is followed by stirring at 85°-95° C. for 5 hours. The suspension is then diluted with 200 parts of water, and the excess bromine is eliminated by gradual addition of 40% strength aqueous sodium bisulfite solution. This is followed by cooling down to 50°-60° C. and the dropwise addition of 25% strength aqueous ammonia solution until a pH value of 9.5 is reached. This is followed by stirring at 50°-60° C. for 4 hours and, finally, by filtration with suction, washing with water until salt-free and drying at 100° C.

The 1,3,6,8-tetrabromopyrene is obtained in an amount of 561 parts and purity of about 84%, which corresponds to a yield of about 90% of theory, based on 100% pure pyrene, and on further processing to naphthalene-1,4,5,8-tetracarboxylic acid in accordance with the instructions of Example 1a 263 parts of naphthalene-1,4,5,8-tetracarboxylic acid 1,4-monoanhydride are obtained.

(b) On adding the bromine not at 40°-50° C. but at 20°-30° C., the subsequent heating gives, on reaching about 40° C., a very violent exothermic reaction which results in a rapid increase in temperature which, when operating on an industrial scale, can lead to a runaway of the temperature and hence to a serious safety risk as a consequence of bromine blowouts.

(c) To reduce the excess of bromine after the bromination A has ended, it is equally possible to use gaseous sulfur dioxide in place of the sodium bisulfite solution.

(d) A tetrabromopyrene which evolves no hydrogen bromide on drying is also obtained when the tetrabromopyrene is, after the reduction of the bromine, isolated by filtration, and, after washing until neutral, is added to 1000 parts of 3% strength aqueous ammonia, which is followed by stirring at 60°-70° C. for 2 hours and subsequently, by renewed filtration with suction, washing with water and drying.

EXAMPLE 4

(a) 220 parts of technical-grade pyrene of 90% purity are added to a solution of 84 parts of sodium chlorate and 350 parts of water.

370 parts of bromine are then added dropwise at 60°-65° C. in 2 hours. This is followed by stirring at 60°-65° C. for 1 hour. The temperature is then raised to 85° C., and 85°-95° C. is maintained with reflux cooling for 10 hours. The tetrabromopyrene is worked up as described in Example 1a.

The 1,3,6,8-tetrabromopyrene (bromine content 61.8%) is obtained in an amount of 557 parts and a purity of about 83%, which corresponds to a yield of about 91% of theory, based on 100% pure pyrene, and on further processing 253 parts of napthalene-1,4,5,8-tetracarboxylic acid 1,4-monoanhydride are obtained.

b) On adding the bromine in Example 4a not at 60°-65° C. but at 70°-75° C., some of the reaction product begins to melt a short time after the beginning of the addition of bromine, forming a greasy mass which in this form is no longer brominatable.

If, by contrast, the bromine is initially added at 60°-65° C. and the temperature is raised to 70°-75° C. only after addition of the bulk of the bromine, then the bromination can be carried out without problems.

c) Using in the bromination described in Example 4a 90 parts of sodium chlorate in place of 84 parts gives tetrabromopyrene of the same quality and yield if the bromine quantity is reduced to 360 parts.

EXAMPLE 5 220 parts of technical-grade pyrene of 90% purity are added to 240 parts of water. 370 parts of bromine are then added dropwise at 35°-40° C. in 2 hours. This is followed by stirring at 35°-40° C. for 1 hour. A solution of 84 parts of sodium chlorate in 100 parts of water is then added dropwise at 45°-55° C. in 1-2 hours. This is followed by stirring at 45°-55° C. for 1 hour and heating to 85° C. and stirring at 85°-95° C. for 6 hours.

The tetrabromopyrene is worked up as described in Example 1a, except that after the ammonia treatment and before the isolation of the tetrabromopyrene the suspension is brought to pH 7 by adding hydrochloric acid.

The 1,3,6,8-tetrabromopyrene (bromine content 61.7%) is obtained in an amount of 556 parts and a purity of about 83%, which corresponds to a yield of about 91% of theory, based on 100% pure pyrene, which on further processing as described in Example 1a produce 252 parts of naphthalene-1,4,5,8-tetracarboxylic acid 1,4-monoanhydride.

EXAMPLE 6

220 parts of technical-grade pyrene of 90% purity are added to a solution of 84 parts of sodium chlorate in 440 parts of water. 380 parts of bromine are then added dropwise at 40°-50° in 2 hours. This is followed by stirring at 40°-50° C. for 1 hour. The reaction vessel is then sealed and the temperature is gradually raised under pressure to 120° C. This is followed by stirring under pressure at 120°-130° C. for 8 hours, cooling down to 60°-70° C. and working up of the tetrabromopyrene as described in Example 1a.

The 1,3,6,8-tetrabromopyrene is obtained in an amount of 556 parts and a purity of about 83%, which corresponds to a yield of about 91% of theory, based on 100% pure pyrene.

EXAMPLE 7

(a) 220 parts of technical-grade pyrene of 90% purity are added to a solution of 84 parts of sodium chlorate in 280 parts of water. 380 parts of bromine are then added dropwise at 40°-50° C. with slight cooling in 2 hours. This is followed by stirring at 40°-50° C. for 1 hour. The temperature is then gradually raised with reflux cooling to 85° C. and stirring at 85°-95° C. for 10 hours. The suspension is worked up as described in Example 1a.

The 1,3,6,8-tetrabromopyrene is obtained in an amount of 564 parts and a purity of about 83%, which corresponds to a yield of about 2% of theory, based on 100% pure pyrene, which on further processing to naphthalene-1,4,5,8-tetracarboxylic acid gives 258 parts of naphthalene-1,4,5,8-tetracarboxylic 1,4-monoanhydride.

(b) Conducting the bromination described in Example 7a in a more pronounced aqueous dilution and using 2000 parts of water instead of 280 parts only gives a yield of 535 parts of 1,3,6,8-tetrabromopyrene, which on further processing as described in Example 1a only give 238 parts of naphthalene-1,4,5,8-tetracarboxylic acid 1,4-monoanhydride.

A similarly unfavorable result is obtained on using 900 parts of water instead of 2000 parts of water.

We claim:

1. A process for preparing 1,3,6,8-tetrabromopyrene by brominating pyrene in aqueous suspension with simultaneous reoxidation of the resulting hydrogen bromide to bromine by means of an oxidizing agent, which comprises reacting pyrene, in a highly concentrated aqueous suspension having a pyrene-water weight ratio of 1:1.2 to 2 with bromine at temperatures of 40° to 65° C. with simultaneous reoxidation of the re$ulting hydrogen bromide to bromine using an oxidizing agent, completing the bromination by heating the reaction mixture to temperatures of 70° to 130° C., reducing excess bromine with a reducing agent to hydrogen bromide and subjecting the 1,3,6,8-tetrabromopyrene formed, preferably without intermediate isolation, to an alkaline aftertreatment at temperatures of 40° to 100° C. within the pH range 8.5 to 12.

2. The process as claimed in claim 1, wherein the pyrene used is technical-grade crude pyrene of 85 to 95% purity.

3. The process as claimed in claim 1, wherein the pyrene-water weight ratio is 1:1.5 to 1.7.

4. The process as claimed in claim 1, wherein the bromination is carried out at temperatures of 45° to 55° C.

5. The process as claimed in claim 1, wherein the resulting hydrogen bromide is reoxidized to bromine by means of alkali metal or alkaline earth metal hypochlorites, hypobromites, peroxodisulfates, chlorates or bromates.

6. The process as claimed in claim 5, wherein the reoxidizing agent used is sodium chlorate.

7. The process as claimed in claim 1, wherein, to carry out the alkaline aftertreatment, the pH value of the reaction mixture is first brought to 6-10 by adding an an alkali metal hydroxide and ammonia is then added in gas form or in the form of an aqueous solution.

* * * * *